US007772277B2

(12) United States Patent
Almarsson et al.

(10) Patent No.: US 7,772,277 B2
(45) Date of Patent: *Aug. 10, 2010

(54) FORMULATIONS COMPRISING FENOFIBRATE AND A STATIN, AND RELATED METHODS OF TREATMENT

(75) Inventors: Orn Almarsson, Shrewsbury, MS (US); Hector Guzman, Jamaica Plain, MA (US); Carolyn Jordan, Charlestown, MA (US); Julius Remenar, Framingham, MA (US)

(73) Assignee: TransForm Pharmaceuticals, Inc., Lexington, MA (US)

( * ) Notice: Subject to any disclaimer, the term of this patent is extended or adjusted under 35 U.S.C. 154(b) by 212 days.

This patent is subject to a terminal disclaimer.

(21) Appl. No.: 11/462,142

(22) Filed: Aug. 3, 2006

(65) Prior Publication Data

US 2007/0032546 A1   Feb. 8, 2007

Related U.S. Application Data

(60) Provisional application No. 60/705,598, filed on Aug. 4, 2005.

(51) Int. Cl.
*A61K 31/315* (2006.01)
*A61K 31/22* (2006.01)
*A61K 31/192* (2006.01)

(52) U.S. Cl. .................. 514/494; 514/547; 514/514; 514/571; 424/400

(58) Field of Classification Search .................. 514/494
See application file for complete search history.

(56) References Cited

U.S. PATENT DOCUMENTS

| 4,231,938 | A | 11/1980 | Monaghan et al. |
|---|---|---|---|
| 4,346,227 | A | 8/1982 | Terahara et al. |
| 4,444,784 | A | 4/1984 | Hoffman et al. |
| 5,177,080 | A | 1/1993 | Angerbauer et al. |
| 5,273,995 | A | 12/1993 | Roth |
| 5,354,772 | A | 10/1994 | Kathawala |
| 6,284,268 | B1* | 9/2001 | Mishra et al. ............... 424/455 |
| 6,316,460 | B1* | 11/2001 | Creekmore et al. ......... 514/275 |
| 2003/0104048 | A1 | 6/2003 | Patel et al. |
| 2003/0153541 | A1* | 8/2003 | Dudley et al. ............... 514/171 |
| 2005/0032878 | A1* | 2/2005 | Deboeck et al. ............. 514/423 |
| 2005/0101561 | A1* | 5/2005 | Tunac ......................... 514/52 |
| 2006/0034815 | A1 | 2/2006 | Guzman et al. |
| 2007/0166413 | A1 | 7/2007 | Haber et al. |

FOREIGN PATENT DOCUMENTS

| EP | 1 336 405 A1 | 8/2003 |
|---|---|---|
| WO | WO 99/29300 A1 | 6/1999 |
| WO | WO 99/29316 A1 | 6/1999 |
| WO | WO 00/57859 A1 | 10/2000 |
| WO | WO 02/43659 * | 6/2002 |
| WO | WO 02/43659 A2 | 6/2002 |
| WO | WO 03/016317 A1 * | 2/2003 |
| WO | WO 2004/002458 A1 | 1/2004 |
| WO | WO 2004/058281 A1 | 7/2004 |

OTHER PUBLICATIONS

Harris (Nonpharmacologic Treatment of hypertriglyceridemia: Fous on fish oils. Clin Cardiol. 22, (Supp II), II-40-II-43(1999)).*
Harris, William S, Clin. Cardiol. 22, (Suppl. II), II-40-II-43 (1999).
International Search Report re:PCT/US2006/030580 dated Dec. 28, 2007.
Grekas et al., "Combined Treatment with Low-Dose Pravastatin and Fish Oil in Post-Renal Transplantation Dislipidemia," *Nephron*, Aug. 2001, vol. 88, No. 4, pp. 329-333.
Yano et al., "Effects of ethyl-all-cis-5,8,11,14,17-icosapentaenoate (epa-e), Paravastatin and their Combination on Serum Lipids and Intimal Thickening of Cuss-Sheathed Carotid Artery in Rabbits," *Life Sciences*, Jan. 1997, vol. 61, No. 20, pp. 2007-2015.
Contacos et al., "Effect of Pravastatin and ω-3 Fatty Acids on Plasma Lipids and Lipoproteins in Patients With Combined Hyperlipidemia," *Arteriosclerosis and Thrombosis*, vol. 13, No. 12, Dec. 1993, pp. 1755-1762.
Supplemental European Search Report of PCT/US2006/030580, dated Sep. 30, 2009.

* cited by examiner

*Primary Examiner*—Jake M. Vu
(74) *Attorney, Agent, or Firm*—RatnerPrestia

(57) ABSTRACT

The invention provides novel omega-3 oil formulations comprising fenofibrate and a statin. These formulations are effective in small volumes. Related methods of treatment are also described.

18 Claims, 7 Drawing Sheets

FORMULATIONS COMPRISING FENOFIBRATE AND A STATIN, AND RELATED METHODS OF TREATMENT

FIELD OF THE INVENTION

The invention provides novel omega-3 oil formulations comprising fenofibrate and a statin. These formulations may be effective pharmaceutical compositions and can be prepared in small volumes.

The invention also provides novel fenofibrate/statin formulations in which fenofibrate is dissolved and a statin is suspended in a vehicle comprising an omega-3 oil, an alcohol, and a surfactant.

BACKGROUND OF THE INVENTION

Fenofibrate (2-[4-(4-chlorobenzoyl)phenoxy]-2-methylpropanoic acid 1-methylethyl ester) is an approved substance for the treatment of hypercholesterolemia and hypertriglyceridemia. Fenofibrate is practically insoluble in water. It is normally poorly and variably absorbed in the fasted state and currently is prescribed to be taken with food.

Known fenofibrate dosage forms include Tricor® micronized tablets in which fenofibrate powder is co-micronized with a solid wetting agent such as sodium lauryl sulfate.

U.S. application Ser. No. 11/573,237 (Almarsson et al.) discloses liquid formulations for treating hypertriglyceridemia which comprise fenofibrate and a mixture of omega-3 oil, an alcohol, and, optionally, one or more surfactants. The disclosed formulations provide fenofibrate formulations in small volumes, due to the attained high concentration of fenofibrate.

The hypotriglyceridemic effects of omega-3 oils from fish oils are well established. Amounts both above and below about 1 gram per day of omega-3 oils from fish oil have been shown to decrease serum triglyceride concentrations by about 25% to about 40%, decrease VLDL blood plasma levels, and to increase both LDL and HDL plasma levels (See e.g., Harris, William S, Clin. Cardiol. 22, (Suppl. II), II-40-II-43 (1999)).

Additionally, it has been clear for several decades that elevated blood cholesterol is a major risk factor for coronary heart disease (CHD), and many studies have shown that the risk of CHD events can be reduced by lipid-lowering therapy. Prior to 1987, the lipid-lowering armamentarium was limited essentially to a low saturated fat and cholesterol diet, the bile acid sequestrants (cholestyramine and colestipol), nicotinic acid (niacin), the fibrates and probucol. Unfortunately, all of these treatments have limited efficacy or tolerability, or both. With the introduction of lovastatin (MEVACOR®; see U.S. Pat. No. 4,231,938), the first inhibitor of HMG-CoA reductase to become available for prescription in 1987, for the first time physicians were able to obtain comparatively large reductions in plasma cholesterol with very few adverse effects.

In addition to the natural fermentation products, mevastatin and lovastatin, there are now a variety of semi-synthetic and totally synthetic HMG-CoA reductase inhibitors, including simvastatin (ZOCOR®; see U.S. Pat. No. 4,444,784), pravastatin sodium salt (PRAVACHOL®; see U.S. Pat. No. 4,346,227), fluvastatin sodium salt (LESCOL®; see U.S. Pat. No. 5,354,772), atorvastatin calcium salt (LIPITOR®; see U.S. Pat. No. 5,273,995) and cerivastatin sodium salt (also known as rivastatin; see U.S. Pat. No. 5,177,080). The HMG-CoA reductase inhibitors described above belong to a structural class of compounds which contain a moiety which can exist as either a 3-hydroxy lactone ring or as the corresponding ring opened dihydroxy open-acid, and are often referred to as "statins."

Salts of the dihydroxy open-acid can be prepared, and in fact, as noted above, several of the marketed statins are administered as the dihydroxy open acid salt forms. In addition, several other statin salts have recently been observed (See US Application No. 20060034815, filed on Aug. 5, 2005).

A pharmaceutical formulation comprising the beneficial effects of fenofibrate, a statin, and omega-3 oil could enable both ease of administration and could improve patient compliance where both fenofibrate and a statin are suitable. In addition, the omega-3 oil may lead to even further therapeutic effect than with fenofibrate and a statin alone.

Ideally, such formulations would not exhibit any food effect, thereby providing health care providers and patients with a wide latitude in selecting convenient and effective antihypertriglyceridemic and antihypercholesterolemic dosage regimens.

SUMMARY OF THE INVENTION

The invention provides novel omega-3 oil formulations of fenofibrate and one or more statins. These formulations are effective in small volumes. Notably, because the formulations of the invention contain an omega-3 oil as the major ingredient, they not only provide an antihypercholesterolemic effect and an antihypertriglyceridemic effect due to the active ingredients, they also provide recommended daily dosages of omega-3 oils (i.e., one gram of omega-3 oil per day, as per AHA guidelines), or a portion thereof.

The invention also provides novel fenofibrate and statin formulations in which fenofibrate is dissolved and a statin is suspended in a vehicle comprising an omega-3 oil, a $C_1$ to $C_4$ alcohol, and, optionally, a surfactant.

Because of their high potency, and minimal effective volumes, formulations of the invention can be administered in a dosage form consisting of one or two capsules as defined hereinafter and at least about 400, 450, 500, 600, 700, 800, 900, or 1000 mg per capsule or per dose of an omega-3 oil.

In one embodiment, formulations of the invention comprise an omega-3 oil, wherein the omega-3 oil is an omega-3 alkyl ester, such as an omega-3 ethyl ester.

The invention provides novel surfactant-containing and surfactant-free, omega-3 oil medicaments of fenofibrate and one or more statins. These medicaments are effective in small volumes. Notably, because the medicaments of the invention contain an omega-3 oil as the major ingredient, they not only provide an antihypercholesterolemic effect and an antihypertriglyceridemic effect due to the active ingredients, they also provide recommended daily dosages of omega-3 oils (i.e., one gram of omega-3 oil per day, as per AHA guidelines), or a portion thereof.

The invention also provides novel fenofibrate/statin medicaments in which fenofibrate is dissolved and a statin is suspended in a vehicle comprising an omega-3 oil, a $C_1$ to $C_4$ alcohol, and, optionally, a surfactant.

These and other embodiments are described in greater detail in the following detailed description.

DETAILED DESCRIPTION OF THE INVENTION

Figure 1:
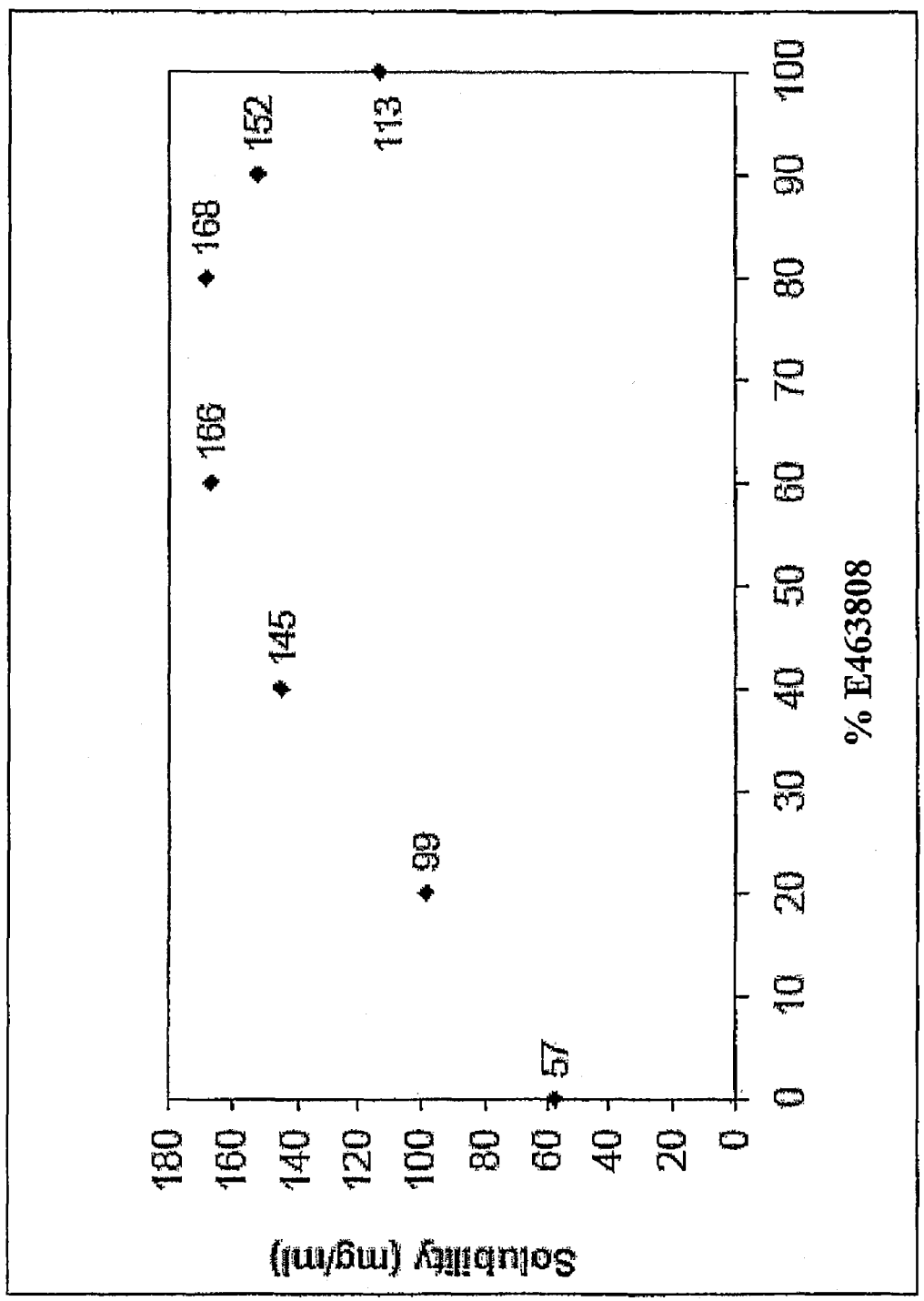
FIG. 1 illustrates the solubility of fenofibrate in E463808-ethanol solutions at 25° C.

The invention provides novel omega-3 oil formulations of fenofibrate and one or more statins. These formulations are effective in small volumes. Notably, because the formulations of the invention contain an omega-3 oil as the major ingredient, they not only provide an antihypercholesterolemic effect and an antihypertriglyceridemic effect due to the active ingredients, they also provide recommended daily dosages of omega-3 oils (i.e., one gram of omega-3 oil per day, as per AHA guidelines), or a portion thereof.

The invention also provides novel fenofibrate and statin formulations in which fenofibrate is dissolved and a statin is suspended in a vehicle comprising an omega-3 oil, a $C_1$ to $C_4$ alcohol, and, optionally, a surfactant.

"$C_1$ to $C_4$ alcohols" include, but are not limited to, methanol, ethanol, propanol, butanol, isopropanol, isobutanol, tert-butanol, glycerol, and propylene glycol.

An "omega-3 oil" is any oil comprising omega-3 fatty acids, omega-3 mono-, di-, or triglycerides, or omega-3 esters including, but not limited to, omega-3 alkyl esters. Omega-3 oils can be characterized using two unique descriptors, species and component. The species of an omega-3 oil is determined by the structure of the polyunsaturated carbon chain bound to the carboxyl group. The component of an omega-3 oil is determined by the chemical nature of the carboxyl group. For example, omega-3 fatty acids employ a —COOH structure bound to the polyunsaturated carbon chain, omega-3 esters employ a —COOR structure bound to the polyunsaturated carbon chain, and omega-3 mono- di- or tri-glycerides employ a —COOR' structure bound to the polyunsaturated carbon chain, where R' comprises a glycerol backbone. Oil composition can be described as both the species and the component(s) of an oil. Such omega-3 oils can be found in, for example, fish oil, marine mammal fat, cod liver oil, walnuts and walnut oil, wheat germ oil, rapeseed oil, soybean lecithin derived oils, soybean derived oils, tofu derived oils, common bean derived oils, butternut derived oils, seaweed derived oils, flax-borage oil, and flax seed oil. Several omega-3 oils which can be used in making formulations of the invention include, but are not limited to, omega-3 oils such as Omegabrite® (Omega Natural Science), Epanova® (Tillotts Pharma AG), OMEGA-3/90 (K D Pharma), Epax® (Pronova Biocare AS), and Incromega (Croda/Bioriginal). The role of specific omega-3 oils in solubilizing fenofibrate is specifically described in co-pending application, U.S. application Ser. No. 11/573,237, which is herein incorporated by reference in its entirety.

"EPA" is defined as eicosapentaenoic acid (C20:5), and "DHA" is defined as docosahexaenoic acid (C22:6). Both EPA and DHA denote only the species of omega-3 oil and do not describe whether the components of such oils exist as, for example, triglycerides, diglycerides, monoglycerides, free acids, esters, or salts.

The term "E107104" is used to describe an omega-3 oil which has a composition comprising 9.7% EPA, 71.4% DHA, and about 3.9% other omega-3 oils (mass percent) where the EPA, DHA, and other omega-3 oils are ethyl esters.

The term "E970002" is used to describe an omega-3 oil which has a composition comprising 97% EPA and about 2% other omega-3 oils (mass percent) where the EPA and other omega-3 oils are ethyl esters.

The term "E351923" is used to describe an omega-3 oil which has a composition comprising 35% EPA (expressed as mass percent of free fatty acids), 19% DHA (expressed as mass percent of free fatty acids), and about 23% other omega-3 oils (mass percent) where the EPA, DHA, and other omega-3 oils are ethyl esters.

The term "E681010" is used to describe an omega-3 oil which has a composition comprising 67.8 percent EPA (mg/g), 9.9 percent DHA (mg/g), and about 9.6 percent other omega-3 oils (mg/g), where the EPA, DHA, and other omega-3 oils are ethyl esters.

The term "E463808" is used to describe an omega-3 oil which has a composition comprising 46% EPA, 38% DHA, and 8% other omega-3 oils (mass percent) where the EPA, DHA, and other omega-3 oils are ethyl esters.

Formulations and medicaments may be described as mixtures of two or more components "by volume," which is herein defined as the volume due to one component divided by the volume of all components of the formulation. This ratio may be converted to or reported as a percentage of the total formulation volume. Such a quantity may also be indicated by "v/v" or "percent v/v." Similarly, the phrases "by weight" and "by mass" describe the weight or mass due to one component divided by the weight or mass of all components of the formulation. This ratio may be converted to or reported as a percentage of the total formulation weight or mass. Such a quantity may also be indicated by "w/w", "mass percent," or "percent w/w."

"Surfactants" refer to a surface active compound which can alter the surface tension of a liquid in which it is dissolved and includes, but is not limited to, Cremophor® EL and Span 20.

In another embodiment, about 5.00, 6.00, 7.00, 8.00, 9.00, 10.00, 11.00, 12.00, 13.00, 14.00, 15.00, 16.00, 17.00, 18.00, 19.00, or 20.00% by volume of an alcohol (for example, ethanol) is included in formulations of the invention to enhance the solubility of fenofibrate in the omega-3 oil.

In another embodiment, the invention provides a formulation comprising less than or equal to about 10.00, 11.00, 12.00, 13.00, 14.00, 15.00, 16.00, 17.00, 18.00, 19.00, 20.00, 21.00, 22.00, 23.00, 24.00 or 25.00% surfactant by weight or by volume.

In another embodiment, a medium-chain triglyceride such as a caprylic/capric triglyceride (e.g., Neobee® M5 Stepan Company) or a medium chain mono-diglyceride such as caprylic/capric mono-diglyceride (e.g., Capmul® MCM, Abitec Corporation) may be included in a formulation of the invention to facilitate digestion of the formulation or reduce the food effect. In another embodiment, a surfactant may be included in a formulation of the invention to enhance digestion of the formulation or reduce the food effect.

According to the present invention, a "statin" includes, but is not limited to, a statin salt. A statin salt includes, but is not limited to, salts of pravastatin, atorvastatin, and fluvastatin. For example, a calcium salt of pravastatin, a magnesium salt of pravastatin, a zinc salt of pravastatin, and a calcium salt of fluvastatin are possible statin salts. See US Application No. 20060034815, which is herein incorporated by reference in its entirety. In another embodiment, a divalent salt of a statin is provided. In another embodiment, the statin salt is amorphous. In another embodiment, the statin salt is crystalline.

In another embodiment, a statin includes other non-salt species, such as simvastatin or cerivastatin, in a free form or another form. Also, non-salt forms of pravastatin, atorvastatin, and fluvastatin may be included in the present invention.

Formulations of the present invention can, optionally, include non-omega-3 oils. For example, one or more non-omega-3 oils can be used in combination with or in place of one or more omega-3 oils in the vehicle for fenofibrate solubilization and statin suspension.

In another embodiment, an omega-3 oil contains a low percentage of non-omega-3 oil. According to the present invention, an omega-3 oil has a low percentage of non-omega-3 oil when it comprises less than about 25.00, 24.00, 23.00, 22.00, 21.00, 20.00, 19.00, 18.00, 17.00, 16.00, 15.00, 14.00, 13.00, 12.00, 11.00, 10.00, 9.00, 8.00, 7.00, 6.00, 5.00, 4.00, 3.00, 2.00, or 1.00 percent w/w non-omega-3 oil. For example, an omega-3 ethyl ester can comprise about 90 percent omega-3 ethyl esters and about 10 percent non-omega-3 ethyl esters.

The purity of omega-3 oil is an important aspect of the present invention. Oil purity is defined as a percentage (e.g., by volume or by weight) of one component of the oil with respect to the entire oil composition. For example, an ester oil with a purity of 95 percent by weight comprises at least 95 percent w/w esters. The remaining percentage may comprise free acids, mono- di- and/or triglycerides, or other components. As another example, an omega-3 ester oil with a purity of 90 percent by weight comprises at least 90 percent omega-3 esters and the remaining percentage can comprise any one or more of other oil components. A mixture of species of one component (e.g., $C_8$ and $C_{10}$ esters) need not be discerned in the determination of purity. However, a distinction of specific species within a component (e.g., $C_8$ and $C_{10}$ esters) can also be included in specific embodiments of the present invention.

According to the present invention, omega-3 oils with a purity greater than about 85.00 percent, 90.00 percent, 91.00 percent, 92.00 percent, 93.00 percent, 94.00 percent, 95.00 percent, 96.00 percent, 97.00 percent, 98.00 percent, 99.00 percent or more can be used, for example, in a pharmaceutical composition. Omega-3 oils, for example with a high purity of omega-3 esters, can be used. According to the present invention, omega-3 oils with a high purity comprise greater than about 85.00 percent, 90.00 percent, 91.00 percent, 92.00 percent, 93.00 percent, 94.00 percent, 95.00 percent, 96.00 percent, 97.00 percent, 98.00 percent, 99.00 percent or more of one component of omega-3 oil by weight or by volume.

In another embodiment, the purity of omega-3 esters or omega-3 alkyl esters is at least about 50.00 percent by weight, at least about 60.00 percent by weight, at least about 70.00 percent by weight, at least about 75.00 percent by weight, at least about 80.00 percent by weight, or at least about 85.00 percent by weight. In another embodiment, the purity of omega-3 esters or omega-3 alkyl esters is about 25.00, 30.00, 35.00, 40.00, 45.00, 50.00, 55.00, 60.00, 65.00, 70.00, 75.00, 80.00, 85.00, 90.00, 95.00, 99.00 percent or more by weight. In another embodiment, the purity of omega-3 esters or omega-3 alkyl esters is between about 25.00 and about 100.00 percent by weight, between about 40.00 and about 100.00 percent by weight, between about 50.00 and about 100.00 percent by weight, between about 60.00 and about 100.00 percent by weight, between about 70.00 and about 100.00 percent by weight, between about 75.00 and about 100.00 percent by weight, between about 75.00 and about 95.00 percent by weight, between about 75.00 and about 90.00 percent by weight, or between about 80.00 and about 85.00 percent by weight. In another embodiment, the purity of omega-3 esters or omega-3 alkyl esters is about 100.00 percent by weight, about 99.00 percent by weight, about 96.00 percent by weight, about 92.00 percent by weight, about 90.00 percent by weight, about 85.00 percent by weight, about 80.00 percent by weight, about 75.00 percent by weight, about 70.00 percent by weight, about 65.00 percent by weight, about 60.00 percent by weight, about 55.00 percent by weight, or about 50.00 percent by weight.

In another embodiment, the omega-3 oil composition comprises EPA and DHA in an amount of at least about 50.00 percent by weight, at least about 60.00 percent by weight, at least about 70.00 percent by weight, at least about 75.00 percent by weight, at least about 80.00 percent by weight, or at least about 84.00 percent by weight of the total omega-3 oil composition. In another embodiment, the omega-3 oil composition comprises EPA and DHA in an amount of about 25.00, 30.00, 35.00, 40.00, 45.00, 50.00, 55.00, 60.00, 65.00, 70.00, 75.00, 80.00, 85.00, 90.00, or 95.00 percent by weight of the total omega-3 oil composition. In another embodiment, the omega-3 oil composition comprises EPA and DHA in an amount of between about 25.00 and about 95.00 percent by weight, between about 40.00 and about 95.00 percent by weight, between about 50.00 and about 95.00 percent by weight, between about 60.00 and about 95.00 percent by weight, between about 70.00 and about 95.00 percent by weight, between about 75.00 and about 95.00 percent by weight, between about 75.00 and about 90.00 percent by weight, between about 75.00 and about 85.00 percent by weight, or between about 80.00 and about 85.00 percent by weight of the total omega-3 oil composition. In another embodiment, the omega-3 oil composition comprises EPA and DHA in an amount of about 99.00 percent by weight, about 96.00 percent by weight, about 92.00 percent by weight, about 90.00 percent by weight, about 84.00 percent by weight, about 80.00 percent by weight, about 75.00 percent by weight, about 70.00 percent by weight, about 65.00 percent by weight, about 60.00 percent by weight, about 55.00 percent by weight, or about 50.00 percent by weight of the total omega-3 oil composition.

In another embodiment, the omega-3 oil has about a 23:19 ratio of EPA:DHA, about a 75:11 ratio of EPA:DHA, about a 95:1 ratio of EPA:DHA, about a 9:2 ratio of EPA:DHA, about a 10:1 ratio of EPA:DHA, about a 5:1 ratio of EPA:DHA, about a 3:1 ratio of EPA:DHA, about a 2:1 ratio of EPA:DHA, about a 1:1 ratio of EPA:DHA, about a 1:2 ratio of EPA:DHA, about a 1:3 ratio of EPA:DHA, or about a 1:5 ratio of EPA:DHA. In another embodiment, the omega-3 oil has about a 95:1 ratio of EPA:DHA, about a 75:1 ratio of EPA:DHA, about a 50:1 ratio of EPA:DHA, about a 25:1 ratio of EPA:DHA, about a 20:1 ratio of EPA:DHA, about a 15:1 ratio of EPA:DHA, about a 10:1 ratio of EPA:DHA, about a 7.5:1 ratio of EPA:DHA, about a 5:1 ratio of EPA:DHA, about a 4:1 ratio of EPA:DHA, about a 3:1 ratio of EPA:DHA, about a 2:1 ratio of EPA:DHA, about a 1.5:1 ratio of EPA:DHA, about a 1:1 ratio of EPA:DHA, about a 1:1.5 ratio of EPA:DHA, about a 1:2 ratio of EPA:DHA, about a 1:3 ratio of EPA:DHA, or about a 1:5 ratio of EPA:DHA. In another embodiment, the omega-3 oil has from about a 95:1 ratio to about a 1:5 ratio of EPA:DHA, from about a 50:1 ratio to about a 1:1 ratio of EPA:DHA, from about a 25:1 ratio to about a 1:1 ratio of EPA:DHA, from about a 10:1 ratio to about a 1:1 ratio of EPA:DHA, from about a 5:1 ratio to about a 1:1 ratio of EPA:DHA, from about a 3:1 ratio to about a 1:1 ratio of EPA:DHA, from about a 2:1 ratio to about a 1:1 ratio of EPA:DHA, or from about a 1.5:1 ratio to about a 1:1 ratio of EPA:DHA. In another embodiment, the omega-3 oil has at least about a 1:5 ratio of EPA:DHA, at least about a 1:1 ratio of EPA:DHA, at least about a 1.5:1 ratio of EPA:DHA, at least about a 2:1 ratio of EPA:DHA, at least about a 3:1 ratio of EPA:DHA, at least about a 5:1 ratio of EPA:DHA, or at least about a 10:1 ratio of EPA:DHA.

An alcohol content of about 10.00, 15.00, 20.00, 25.00, 30.00, 35.00, or 40.00 percent by volume has been shown to enhance fenofibrate solubilization (See PCT WO2006/017602 U.S. application Ser. No. 11/573,237). For example, such an alcohol is ethanol. Another alcohol is glycerol. Alcohols may have one, two, or three or more —OH groups per molecule.

In another embodiment, a formulation of the present invention comprises one or more statins, fenofibrate, and an omega-3 oil. In another embodiment, the formulation is a suspension of particles of one or more statins in a solution of omega-3 oil, a $C_1$ to a $C_4$ alcohol, and fenofibrate. See e.g., US Application No. 20060034815.

In another embodiment, the invention provides a formulation comprising about 65.00, 66.00, 67.00, 68.00, 69.00, 70.00, 71.00, 72.00, 73.00, 74.00, 75.00, 76.00, 77.00, 78.00, 79.00, 80.00, 81.00, 82.00, 83.00, 84.00, or 85.00% by weight of an omega-3 oil, about 5.00, 6.00, 7.00, 8.00, 9.00, 10.00, 11.00, 12.00, 13.00, 14.00, or 15.00% by weight of a $C_1$ to $C_4$ alcohol, about 10.00, 11.00, 12.00, 13.00, 14.00, 15.00, 16.00, 17.00, 18.00, 19.00, 20.00, 21.00, 22.00, 23.00, 24.00, or 25.00% by weight of one or more statins, and about 10.00, 11.00, 12.00, 13.00, 14.00, 15.00, 16.00, 17.00, 18.00, 19.00, or 20.00% by weight of fenofibrate.

In another embodiment, the invention provides a formulation comprising about 65.00, 66.00, 67.00, 68.00, 69.00, 70.00, 71.00, 72.00, 73.00, 74.00, 75.00, 76.00, 77.00, 78.00, 79.00, 80.00, 81.00, 82.00, 83.00, 84.00, or 85.00% by weight of an omega-3 oil, about 5.00, 6.00, 7.00, 8.00, 9.00, 10.00, 11.00, 12.00, 13.00, 14.00, or 15.00% by weight of a $C_1$ to $C_4$ alcohol, about 10.00, 11.00, 12.00, 13.00, 14.00, 15.00, 16.00, 17.00, 18.00, 19.00, 20.00, 21.00, 22.00, 23.00, 24.00, or 25.00% by weight of one or more salts of pravastatin, and about 10.00, 11.00, 12.00, 13.00, 14.00, 15.00, 16.00, 17.00, 18.00, 19.00, or 20.00% by weight of fenofibrate.

In another embodiment, the invention provides a formulation comprising about 65.00, 66.00, 67.00, 68.00, 69.00, 70.00, 71.00, 72.00, 73.00, 74.00, 75.00, 76.00, 77.00, 78.00, 79.00, 80.00, 81.00, 82.00, 83.00, 84.00, or 85.00% by weight of an omega-3 oil, about 5.00, 6.00, 7.00, 8.00, 9.00, 10.00, 11.00, 12.00, 13.00, 14.00, or 15.00% by weight of a $C_1$ to $C_4$ alcohol, about 10.00, 11.00, 12.00, 13.00, 14.00, 15.00, 16.00, 17.00, 18.00, 19.00, 20.00, 21.00, 22.00, 23.00, 24.00, or 25.00% by weight of one or more salts of fluvastatin, and about 10.00, 11.00, 12.00, 13.00, 14.00, 15.00, 16.00, 17.00, 18.00, 19.00, or 20.00% by weight of fenofibrate.

In another embodiment, the invention provides a formulation comprising about 65.00, 66.00, 67.00, 68.00, 69.00, 70.00, 71.00, 72.00, 73.00, 74.00, 75.00, 76.00, 77.00, 78.00, 79.00, 80.00, 81.00, 82.00, 83.00, 84.00, or 85.00% by weight of an omega-3 oil, about 5.00, 6.00, 7.00, 8.00, 9.00, 10.00, 11.00, 12.00, 13.00, 14.00, or 15.00% by weight of a $C_1$ to $C_4$ alcohol, about 10.00, 11.00, 12.00, 13.00, 14.00, 15.00, 16.00, 17.00, 18.00, 19.00, 20.00, 21.00, 22.00, 23.00, 24.00, or 25.00% by weight of one or more salts of atorvastatin, and about 10.00, 11.00, 12.00, 13.00, 14.00, 15.00, 16.00, 17.00, 18.00, 19.00, or 20.00% by weight of fenofibrate.

In another embodiment, the invention provides a formulation comprising about 65.00, 66.00, 67.00, 68.00, 69.00, 70.00, 71.00, 72.00, 73.00, 74.00, 75.00, 76.00, 77.00, 78.00, 79.00, 80.00, 81.00, 82.00, 83.00, 84.00, or 85.00% by weight of an omega-3 oil, about 5.00, 6.00, 7.00, 8.00, 9.00, 10.00, 11.00, 12.00, 13.00, 14.00, or 15.00% by weight of a $C_1$ to $C_4$ alcohol, about 10.00, 11.00, 12.00, 13.00, 14.00, 15.00, 16.00, 17.00, 18.00, 19.00, 20.00, 21.00, 22.00, 23.00, 24.00, or 25.00% by weight simvastatin, and about 10.00, 11.00, 12.00, 13.00, 14.00, 15.00, 16.00, 17.00, 18.00, 19.00, or 20.00% by weight of fenofibrate.

In another embodiment, the invention provides a formulation comprising about 65.00, 66.00, 67.00, 68.00, 69.00, 70.00, 71.00, 72.00, 73.00, 74.00, 75.00, 76.00, 77.00, 78.00, 79.00, 80.00, 81.00, 82.00, 83.00, 84.00, or 85.00% by weight of an omega-3 ester or omega-3 alkyl ester, about 5.00, 6.00, 7.00, 8.00, 9.00, 10.00, 11.00, 12.00, 13.00, 14.00, or 15.00% by weight of a $C_1$ to $C_4$ alcohol, about 10.00, 11.00, 12.00, 13.00, 14.00, 15.00, 16.00, 17.00, 18.00, 19.00, 20.00, 21.00, 22.00, 23.00, 24.00, or 25.00% by weight of one or more statins, and about 10.00, 11.00, 12.00, 13.00, 14.00, 15.00, 16.00, 17.00, 18.00, 19.00, or 20.00% by weight of fenofibrate.

In another embodiment, the invention provides a formulation comprising about 65.00, 66.00, 67.00, 68.00, 69.00, 70.00, 71.00, 72.00, 73.00, 74.00, 75.00, 76.00, 77.00, 78.00, 79.00, 80.00, 81.00, 82.00, 83.00, 84.00, or 85.00% by weight of an omega-3 ester or omega-3 alkyl ester, about 5.00, 6.00, 7.00, 8.00, 9.00, 10.00, 11.00, 12.00, 13.00, 14.00, or 15.00% by weight of a $C_1$ to $C_4$ alcohol, about 10.00, 11.00, 12.00, 13.00, 14.00, 15.00, 16.00, 17.00, 18.00, 19.00, 20.00, 21.00, 22.00, 23.00, 24.00, or 25.00% by weight of one or more salts of pravastatin, and about 10.00, 11.00, 12.00, 13.00, 14.00, 15.00, 16.00, 17.00, 18.00, 19.00, or 20.00% by weight of fenofibrate.

In another embodiment, the invention provides a formulation comprising about 65.00, 66.00, 67.00, 68.00, 69.00, 70.00, 71.00, 72.00, 73.00, 74.00, 75.00, 76.00, 77.00, 78.00, 79.00, 80.00, 81.00, 82.00, 83.00, 84.00, or 85.00% by weight of an omega-3 ester or omega-3 alkyl ester, about 5.00, 6.00, 7.00, 8.00, 9.00, 10.00, 11.00, 12.00, 13.00, 14.00, or 15.00% by weight of a $C_1$ to $C_4$ alcohol, about 10.00, 11.00, 12.00, 13.00, 14.00, 15.00, 16.00, 17.00, 18.00, 19.00, 20.00, 21.00, 22.00, 23.00, 24.00, or 25.00% by weight of one or more salts of fluvastatin, and about 10.00, 11.00, 12.00, 13.00, 14.00, 15.00, 16.00, 17.00, 18.00, 19.00, or 20.00% by weight of fenofibrate.

In another embodiment, the invention provides a formulation comprising about 65.00, 66.00, 67.00, 68.00, 69.00, 70.00, 71.00, 72.00, 73.00, 74.00, 75.00, 76.00, 77.00, 78.00, 79.00, 80.00, 81.00, 82.00, 83.00, 84.00, or 85.00% by weight of an omega-3 ester or omega-3 alkyl ester, about 5.00, 6.00, 7.00, 8.00, 9.00, 10.00, 11.00, 12.00, 13.00, 14.00, or 15.00% by weight of a $C_1$ to $C_4$ alcohol, about 10.00, 11.00, 12.00, 13.00, 14.00, 15.00, 16.00, 17.00, 18.00, 19.00, 20.00, 21.00, 22.00, 23.00, 24.00, or 25.00% by weight of one or more salts of atorvastatin, and about 10.00, 11.00, 12.00, 13.00, 14.00, 15.00, 16.00, 17.00, 18.00, 19.00, or 20.00% by weight of fenofibrate.

In another embodiment, the invention provides a formulation comprising about 65.00, 66.00, 67.00, 68.00, 69.00, 70.00, 71.00, 72.00, 73.00, 74.00, 75.00, 76.00, 77.00, 78.00, 79.00, 80.00, 81.00, 82.00, 83.00, 84.00, or 85.00% by weight of an omega-3 ester or omega-3 alkyl ester, about 5.00, 6.00, 7.00, 8.00, 9.00, 10.00, 11.00, 12.00, 13.00, 14.00, or 15.00% by weight of a $C_1$ to $C_4$ alcohol, about 10.00, 11.00, 12.00, 13.00, 14.00, 15.00, 16.00, 17.00, 18.00, 19.00, 20.00, 21.00, 22.00, 23.00, 24.00, or 25.00% by weight simvastatin, and about 10.00, 11.00, 12.00, 13.00, 14.00, 15.00, 16.00, 17.00, 18.00, 19.00, or 20.00% by weight of fenofibrate.

In another embodiment, formulations of the present invention can be used as pharmaceutical compositions or medicaments.

Formulations of the invention can become chemically unstable under conditions of elevated temperature and/or relative humidity. Formulations of the present invention are generally manufactured and stored at temperatures at or below about 30 degrees C. to prevent chemical degradation prior to administration.

A formulation of the invention which includes a combination of a statin, fenofibrate, and an omega-3 oil, is effective in preventing, reducing and/or treating elevated cholesterol levels (such as in hypercholesterolemia), elevated triglyceride levels (such as hypertriglyceridemia), atherosclerosis, cardiovascular events and disease including coronary events and cerebrovascular events, and coronary artery disease and/or cerebrovascular disease.

In another embodiment, a method of preventing, reducing, and/or treating elevated cholesterol levels (such as in hypercholesterolemia), atherosclerosis, hypertriglyceridemia, cardiovascular events and disease including coronary events and cerebrovascular events, and coronary artery disease and/or cerebrovascular disease is provided. This method comprises administering an effective amount of a formulation of the present invention to a mammal in need of such prevention, reduction, and/or treatment. In another embodiment, the mammal is a human.

The formulations of the present invention can be prepared according to any one or more methods available in the art. For example, in one embodiment comprising omega-3 oil, fenofibrate, a statin or a salt thereof, ethanol, and, optionally, one or more surfactants, appropriate amounts of said formulation components can be mixed together at room temperature or at a slightly elevated temperature. Where one or more formulation components contain a solid which has precipitated from solution (e.g., a surfactant), such a component can be heated and mixed so as to induce resolubilization prior to combining with the remaining formulation components.

A therapeutically acceptable daily dosage of omega-3 oil has been recommended or considered via several national and international groups including, but not limited to, the American Heart Association (AHA) and the International Society for the Study of Fatty Acids and Lipids (ISSFAL). Table 1 includes daily dosage amounts of omega-3 oil as considered/recommended via several organizations.

TABLE 1

Daily dosages of omega-3 oil

| Omega-3 oil dose (grams)/day | Comment |
|---|---|
| 0.65 | ISSFAL consideration (1999) |
| 1.0 | AHA recommended (2000, 2004) |
| 1.8 | Omacor ® dose |
| 3.0 | FDA limit on daily consumption, general population |
| 3.6 | Omacor ® dose |

Typical dosage forms of the invention comprise from about 10 mg to about 200 mg, or an amount of from about 25 mg to about 200 mg, or an amount of from 40 mg to 200 mg, or an amount of from about 50 mg to about 200 mg of fenofibrate. For example, dosage forms comprising 30, 40, 50, 60, 70, 80, 90, 100, 110, 120, 130, 140, 145, 150, 160, 170, 180, 190, or 200 mg fenofibrate are included. More specifically, doses include 50, 100, 145, 150, and 160 mg of fenofibrate.

Typical dosage forms of the invention also comprise from about 1 mg to about 160 mg, preferably in an amount of from about 5 mg to about 160 mg of a statin. For example, dosage forms comprising 5, 10, 15, 20, 25, 30, 35, 40, 45, 50, 55, 60, 65, 70, 75, 80, 90, 100, 110, 120, 130, 140, 150, or 160 mg are preferable. The dosage amounts described herein are expressed in amounts of statin free base and do not include the weight of a counterion (e.g., zinc) or any water or solvent molecules.

Formulations of the present invention, optionally, can be administered in soft gelatin capsules. Such soft gelatin capsules can be in any shape, for example, oval or oblongs. The volume of such capsules can be between about 0.5 mL and about 1.5 mL. For example, about 0.50, 0.55, 0.60, 0.65, 0.70, 0.75, 0.80, 0.85, 0.90, 0.95, 1.00, 1.05, 1.10, 1.15, 1.20, 1.25, 1.30, 1.35, 1.40, 1.45, or 1.50 mL. In one embodiment, one dose is administered in a single capsule. In another embodiment, one dose is administered in two capsules. In another embodiment, one dose is administered in three or more capsules. Optionally, each dose can be packaged individually in a blister-pack. In another embodiment, the soft gelatin material is both chemically and physically stable while in contact with a formulation of the invention. In another embodiment, the soft gelatin material prevents the alcohol in the formulation from escaping the capsule. In another embodiment, the soft gelatin material prevents a significant amount of the alcohol in the formulation from escaping the capsule.

All aforementioned ranges of percent identity are to be taken as including, and providing written description and support for, any fractional percentage, in intervals of 0.01%.

These and other embodiments of the invention are illustrated further in the following examples, which are illustrative and in no way limiting.

EXAMPLES

Example 1

Preparation of Pravastatin Zinc Salt 2 equivalents of pravastatin sodium dissolved in de-ionized water are reacted with a solution having 1 equivalent of zinc chloride in de-ionized water. Precipitation of crystalline pravastatin zinc occurs immediately at room temperature. The resultant salt was a 2:1 pravastatin to zinc salt. The preparation and characterization of pravastatin zinc are described more completely in Example 7 of US Application No. 20060034815.

Example 2

Fenofibrate Solubility in the Presence of Pravastatin Zinc Salt

Two doses of pravastatin zinc were used: 10 mg and 80 mg. 10 mg and 80 mg (weight of active only) correspond to about 13 g, and about 106 g, respectively, for the weight of the zinc salt. Table 2 includes solubility data of fenofibrate and pravastatin zinc in an 87:13 Incromega:ethanol vehicle and in a 70:10:10:10 Incromega:ethanol:Cremophor EL:Span 20 vehicle at 14 and 25 degrees C. (The above ratios are expressed in percent weight.) The solubility measurements in Table 2 were acquired after 3 to 5 days were allowed for equilibration of the formulations to occur. Solubility measurements were obtained via HPLC wherein the sample diluent was 70:30 acetonitrile:deionized water. Samples were diluted by a factor of 1000. (Note: The Incromega oil used in this Example was Incromega E7010 SR by Croda.)

TABLE 2

Fenofibrate Solubility in omega-3 oil formulation with pravastatin zinc

| Sample | Sample Name | Pravastatin Zinc (mg) | Temp (C.) | Fenofibrate Solubility (mg/mL) | Pravastatin Zinc Solubility (mg/mL) |
|---|---|---|---|---|---|
| 1 | 87:13 | 13.8 | 25 | 172 | 0.60 |
| 2 | Incromega: ethanol | 13.7 | 14 | 130 | 0.45 |
| 3 | 87:13 | 105.8 | 25 | 172 | 0.40 |
| 4 | Incromega: ethanol | 106.7 | 14 | 126 | 0.33 |
| 5 | 70:10:10:10 | 13.8 | 25 | 153 | 0.78 |
| 6 | Incromega: ethanol: Cremophor EL: Span 20 | 13.1 | 14 | 108 | 0.68 |
| 7 | 70:10:10:10 | 105.3 | 25 | 144 | 1.09 |
| 8 | Incromega: ethanol: Cremophor EL: Span 20 | 106.8 | 14 | 114 | 1.00 |

Example 3

Solubility of Fenofibrate in Different Liquid Vehicles

Saturated solutions of fenofibrate in various liquid vehicles were prepared in 1.5 mL glass vials by stepwise addition of fenofibrate powder to approximately 0.5-1 mL of liquid vehicle. If the powder dissolved completely, more fenofibrate was added until an excess of powder was observed. The samples were then stirred overnight at 25° C. controlled temperature before being filtered through a 0.2 micrometer PVDF syringe filter. The filtrate was diluted with n-heptane and analyzed via normal phase HPLC.

Table 3 summarizes the solubility of Fenofibrate in various liquid vehicles.

TABLE 3

Solubility of fenofibrate in various liquid vehicles.

| No. | Mixture | Solubility (mg/ml, at 25 degrees C.) |
|---|---|---|
| 1 | 100% E9501EE** | 107 |
| 2 | 100% E463808* | 113 |
| 3 | 90:10 E463808:Ethanol* | 152 |
| 4 | 80:20 E463808:Ethanol* | 168 |
| 5 | 60:40 E463808:Ethanol* | 166 |
| 6 | 40:60 E463808:Ethanol* | 145 |
| 7 | 20:80 E463808:Ethanol* | 99 |
| 8 | 100% Ethanol | 57 |
| 9 | 80:10:10 E463808:Ethanol:Labrafac CC* | 148 |
| 10 | 100% Omegabrite | 113 |
| 11 | 100% Myvacet 9-45 | 115 |
| 12 | 100% Epax 1050TG | 76 |
| 13 | 100% Epax 4510TG | 80 |
| 14 | 100% Cod liver oil | 52 |
| 15 | 100% Natural fish oil | 55 |
| 16 | 100% Flaxseed oil | 57 |
| 17 | 100% Flax-borage | 59 |

*E463808 comprises 46 percent EPA, 38 percent DHA, and 8 percent other omega-3's as ethyl esters (mass percent)
**E9501EE comprises 95 percent EPA, 1 percent DHA, as ethyl esters (mass percent)

Based on available composition data, Table 4 below compares fenofibrate solubility and omega-3 content in different vehicles.

TABLE 4

Fenofibrate solubility and omega-3 content (mass percent) in various vehicles.

| | EPA % | DHA % | Other omega-3 % | Total % | Solubility (mg/mL) at 25 deg C. |
|---|---|---|---|---|---|
| Cod Liver Oil | 11 | 11 | 0 | 22 | 52 |
| Natural Fish Oil | 18 | 12 | 0 | 30 | 55 |
| Flax Seed Oil | 0 | 0 | 50 | 50 | 57 |
| Flax-Borage Oil | 7 | 5 | 50 | 62 | 59 |
| EPAX ® 1050 TG | 10 | 50 | 0 | 60 | 76 |
| EPAX ® 4510 TG | 45 | 10 | 0 | 55 | 80 |
| E9501EE** | 95 | 1 | 0 | 96 | 107 |
| Omegabrite ® | 75 | 11 | 6 | 92 | 113 |
| E463808* | 46 | 38 | 8 | 92 | 113 |

*E463808 comprises 46 percent EPA, 38 percent DHA, and 8 percent other omega-3's (mass percent) as ethyl esters
**E9501EE comprises 95 percent EPA, 1 percent DHA (mass percent) as ethyl esters It is believed that, among other factors, fenofibrate solubility in omega-3 oils may also be proportional to the number of double-bonds present in the vehicle. Using available composition data from E463808 and E9501EE omega-3 oils, Table 5 below shows the estimated moles of double bonds per gram of vehicle and their corresponding fenofibrate solubility:

TABLE 5

Estimated double bonds per gram of vehicle.

| Vehicle | Moles double bond/g | Fenofibrate solubility (mg/ml) |
|---|---|---|
| E463808 | 0.01514 | 113 |
| E9501EE | 0.01506 | 107 |

FIG. 1 shows the solubility of fenofibrate in E463808/Ethanol mixtures at 25° C. FIG. 1 illustrates the effect of ethanol content on fenofibrate solubility in E463808. The solubility profile shows a non-obvious solubility enhancement with a maximum solubility between 10-40% ethanol (v/v). It is unique to observe this type of non-linearity in non-aqueous systems. The increase in fenofibrate solubility in the presence of ethanol was not limited only to E463808. Significant solubility increases were also observed with other omega-3 oils such as those with EPA:DHA ratios of 75:11, 10:50, and 45:10. The 75:11 oil comprises EPA and DHA in ethyl ester form while the 10:50 and 45:10 oils comprise EPA and DHA in triglyceride form.

Example 4

Fenofibrate Solubility in E463808-Based Formulations

Temperature Dependence

It was noted that the solubility of the formulations of Example 3 showed a strong dependence on temperature. The experiment of this example studied this effect in greater detail.

Saturated fenofibrate samples were prepared under three controlled temperatures: 4° C., 23° C., and 33° C. After overnight stirring and incubation, the samples were filtered using a 0.2 micrometer PVDF syringe filter. The filter apparatus was pre-incubated at the sample temperature before use. The filtrates were promptly diluted and analyzed via normal phase HPLC.

Figure 2:
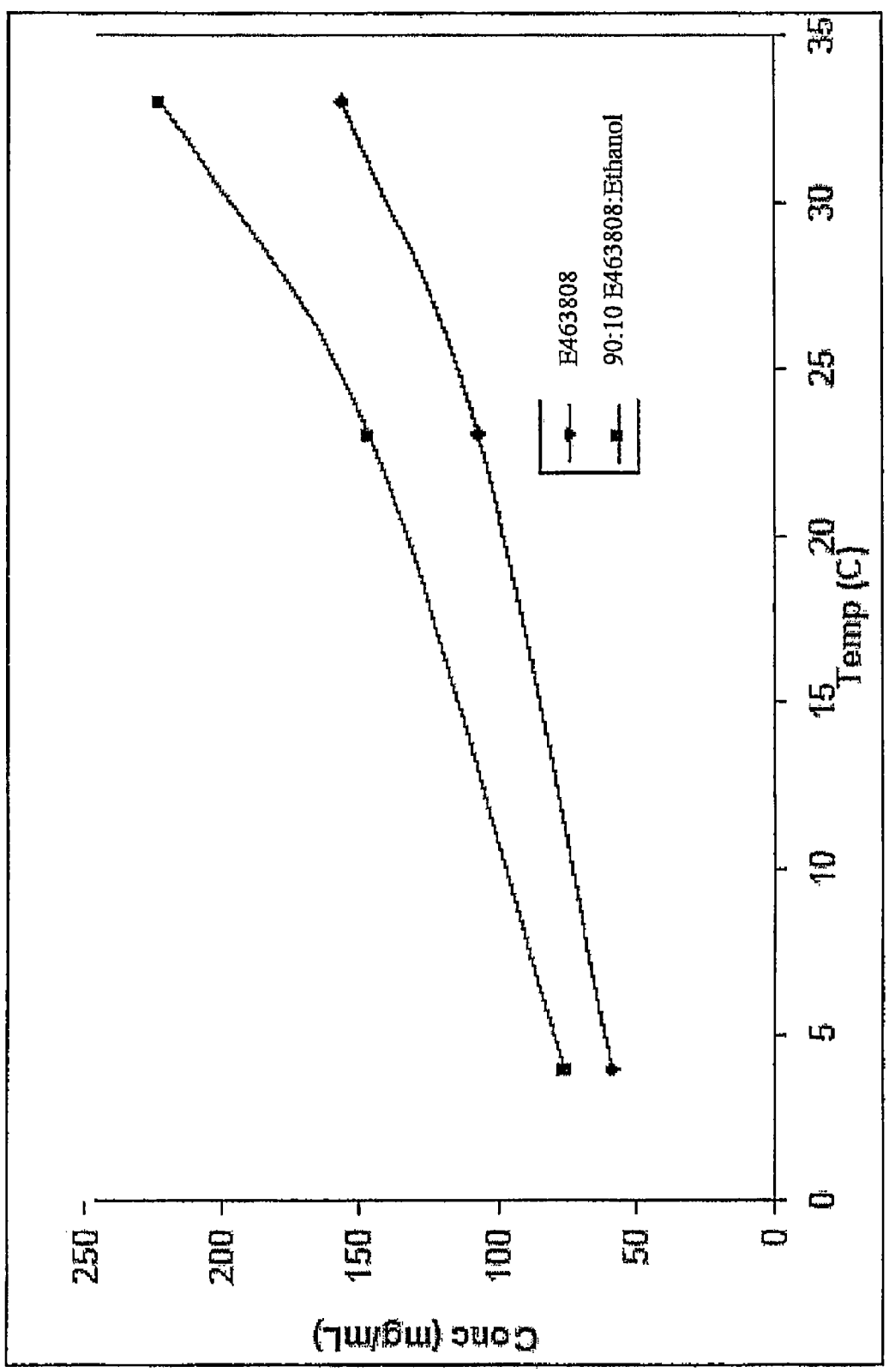
FIG. 2 illustrates the effect of temperature on fenofibrate solubility in pure E463808 and E463808-ethanol solutions.
Figure 3:
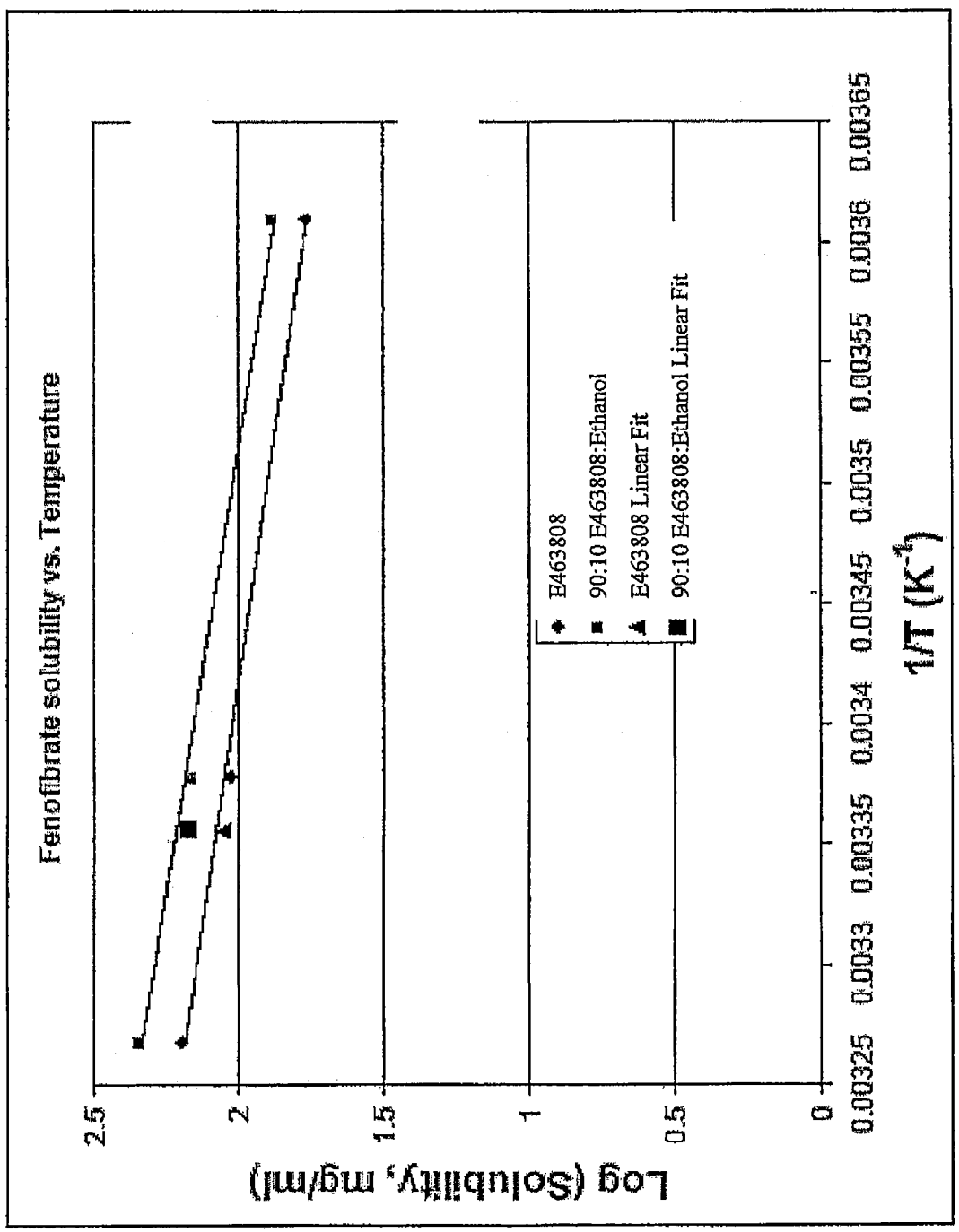
FIG. 3 illustrates the Van't Hoff temperature dependence of fenofibrate solubility in pure E463808 and in E463808-ethanol mixtures.

Fenofibrate solubility versus temperature in two vehicles (100% E463808, and 90:10 E463808:ethanol v/v) were measured and are illustrated in FIG. 2. The solubility of fenofibrate showed a relatively steep dependence on temperature. The Van't Hoff-type plot is illustrated in FIG. 3.

Example 5

Equilibrium Fenofibrate Solubility in Ethyl Esters Versus Triglycerides

Table 6 shows a comparison of fenofibrate solubility in ethyl esters and that in corresponding triglycerides at 25° C. Polarity and the number of C=C double bonds correlate with increased fenofibrate solubility. Importantly, fenofibrate shows higher solubility consistently in ethyl esters than in a corresponding triglyceride.

TABLE 6

Fenofibrate solubility at 25 degrees C. in ethyl esters and triglycerides.

| Vehicle | Description | Solubility (mg/mL) |
|---|---|---|
| Ethyl caprylate | C8, ethyl ester | 177.8 |
| Ethyl caprate | C10, ethyl ester | 142.2 |
| Neobee M5 | C8 and C10, triglyceride | 82.0 |
| Ethyl oleate | C18, 1 double bond, ethyl ester | 86.7 |
| Triolein | C18, 1 double bond, triglyceride | 48.9 |
| Ethyl linoleate | C18, 2 double bonds, ethyl ester | 92.3 |
| Trilinolein | C18, 2 double bonds, triglyceride | 61.2 |

Example 6

Determination of Increased Solubilization Power with Ethanol and Ethyl Esters

A saturated solution of fenofibrate (125.80 mg) in TG361724 fish oil was prepared by adding the fish oil to the fenofibrate up to a volume of 1 mL. The fish oil was comprised of triglycerides. A stir bar was added and the container was crimp sealed. The container was placed in a water bath at 25° C. and stirred overnight. The sample was then filtered through a 0.2 micrometer PVDF syringe filter, the liquid was collected and diluted in ethanol by a factor of 2000. A UV spectrophotometer (285 nm) was used to measure the fenofibrate concentration. The solubility of fenofibrate in pure TG361724 is reported below in Table 7.

A saturated solution of fenofibrate (145.47 mg) in a 90:10 solution by volume of TG361724: ethanol was prepared by adding the fish oil:ethanol mixture to the fenofibrate up to a volume of 1 mL. The fish oil was comprised of triglycerides. A stir bar was added and the container was crimp sealed. The container was placed in a water bath at 25° C. and stirred overnight. The sample was then filtered through a 0.2 micrometer PVDF syringe filter, the liquid was collected and diluted in ethanol by a factor of 2000. A UV spectrophotometer (285 nm) was used to measure the fenofibrate concentration. The solubility of fenofibrate in a mixture of 90:10 TG361724:ethanol is reported below in Table 7.

A saturated solution of fenofibrate (125.46 mg) in E351923 was prepared by adding the fish oil to the fenofibrate up to a volume of 1 mL. The fish oil was comprised of ethyl esters. A stir bar was added and the container was crimp sealed. The container was placed in a water bath at 25° C. and stirred overnight. The sample was then filtered through a 0.2 micrometer PVDF syringe filter, the liquid was collected and diluted in ethanol by a factor of 2000. A UV spectrophotometer (285 nm) was used to measure the fenofibrate concentration. The solubility of fenofibrate in pure E351923 is reported below in Table 7.

A saturated solution of fenofibrate (201.74 mg) in a 90:10 solution by volume of E351923:ethanol was prepared by adding the fish oil:ethanol mixture to the fenofibrate up to a volume of 1 mL. The fish oil was comprised of ethyl esters. A stir bar was added and the container was crimp sealed. The container was placed in a water bath at 25° C. and stirred overnight. The sample was then filtered through a 0.2 micrometer PVDF syringe filter, the liquid was collected and diluted in ethanol by a factor of 2000. A UV spectrophotometer (285 nm) was used to measure the fenofibrate concentration. The solubility of fenofibrate in a mixture of 90:10 E351923:ethanol is reported below in Table 7.

TABLE 7

Fenofibrate solubility in several oils and oil:ethanol mixtures at 25 degrees C.

| Liquid Vehicle | Solubility (mg/mL) |
|---|---|
| TG361724 | 67.3 |
| 90:10 TG361724:ethanol | 88.5 |
| E351923 | 95.6 |
| 90:10 E351923:ethanol | 129.0 |

A saturated solution of fenofibrate (130.9 mg) in E107104 was prepared by adding the fish oil to the fenofibrate up to a volume of 1 mL. The fish oil was rich in DHA. A stir bar was added and the container was crimp sealed. The container was placed in a water bath at 25° C. and stirred overnight. The sample was then filtered through a 0.2 micrometer PVDF syringe filter, the liquid was collected and diluted in ethanol by a factor of 2000. A UV spectrophotometer (285 nm) was used to measure the fenofibrate concentration. The solubility of fenofibrate in pure E107104 is reported below in Table 8.

A saturated solution of fenofibrate (151.3 mg) in a 95:5 solution by volume of E107104:ethanol was prepared by adding the fish oil:ethanol mixture to the fenofibrate up to a volume of 1 mL. The fish oil was rich in DHA. A stir bar was added and the container was crimp sealed. The container was placed in a water bath at 25° C. and stirred overnight. The sample was then filtered through a 0.2 micrometer PVDF syringe filter, the liquid was collected and diluted in ethanol by a factor of 2000. A UV spectrophotometer (285 nm) was used to measure the fenofibrate concentration. The solubility of fenofibrate in a mixture of 95:5 E107104:ethanol is reported below in Table 8.

A saturated solution of fenofibrate (161.6 mg) in a 90:10 solution by volume of E107104:ethanol was prepared by adding the fish oil:ethanol mixture to the fenofibrate up to a volume of 1 mL. The fish oil was rich in DHA. A stir bar was added and the container was crimp sealed. The container was placed in a water bath at 25° C. and stirred overnight. The sample was then filtered through a 0.2 micrometer PVDF syringe filter, the liquid was collected and diluted in ethanol by a factor of 2000. A UV spectrophotometer (285 nm) was used to measure the fenofibrate concentration. The solubility of fenofibrate in a mixture of 90:10 E107104:ethanol is reported below in Table 8.

A saturated solution of fenofibrate (154.2 mg) in E970002 was prepared by adding the fish oil to the fenofibrate up to a volume of 1 mL. The fish oil was rich in EPA. A stir bar was added and the container was crimp sealed. The container was placed in a water bath at 25° C. and stirred overnight. The sample was then filtered through a 0.2 micrometer PVDF syringe filter, the liquid was collected and diluted in ethanol by a factor of 2000. A UV spectrophotometer (285 nm) was used to measure the fenofibrate concentration. The solubility of fenofibrate in pure E970002 is reported below in Table 8.

A saturated solution of fenofibrate (204.8 mg) in a 90:10 solution by volume of E970002:ethanol was prepared by adding the fish oil:ethanol mixture to the fenofibrate up to a volume of 1 mL. The fish oil was rich in EPA. A stir bar was added and the container was crimp sealed. The container was placed in a water bath at 25° C. and stirred overnight. The sample was then filtered through a 0.2 micrometer PVDF syringe tilter, the liquid was collected and diluted in ethanol by a factor of 2000. A UV spectrophotometer (285 nm) was used to measure the fenofibrate concentration. The solubility of fenofibrate in a mixture of 90:10 E970002:ethanol is reported below in Table 8.

TABLE 8

Fenofibrate solubility in several EPA and DHA-rich oils and oil:ethanol mixtures at 25 degrees C.

| Liquid Vehicle | Solubility (mg/mL) |
|---|---|
| E107104 | 102.2 |
| 95:5 E107104:ethanol | 124.5 |
| 90:10 E107104:ethanol | 132.1 |
| E970002 | 106.7 |
| 90:10 E970002:ethanol | 140.8 |

Table 7 shows an increased solubility of fenofibrate in omega-3 oils when ethanol is added to the formulation. Although this increase is seen in omega-3 triglyceride-based oils as well as omega-3 ethyl ester-based oils, it is only the ethyl ester-based omega-3 oils that provide the fenofibrate solubility at and above 100 mg/mL which is necessary for liquid formulations of the present invention. Table 8 shows a similar increase in fenofibrate solubility with the addition of ethanol. Also, omega-3 oils with a high content of DHA and omega-3 oils with a high content of EPA both provide similar solubilization power. Based on the above data, the ratio of EPA:DHA does not appear to be a critical variable for the increased solubilization power of fenofibrate in omega-3 oil.

Example 7

Fenofibrate Solubility as a Function of Ethanol Concentration

Figure 4:
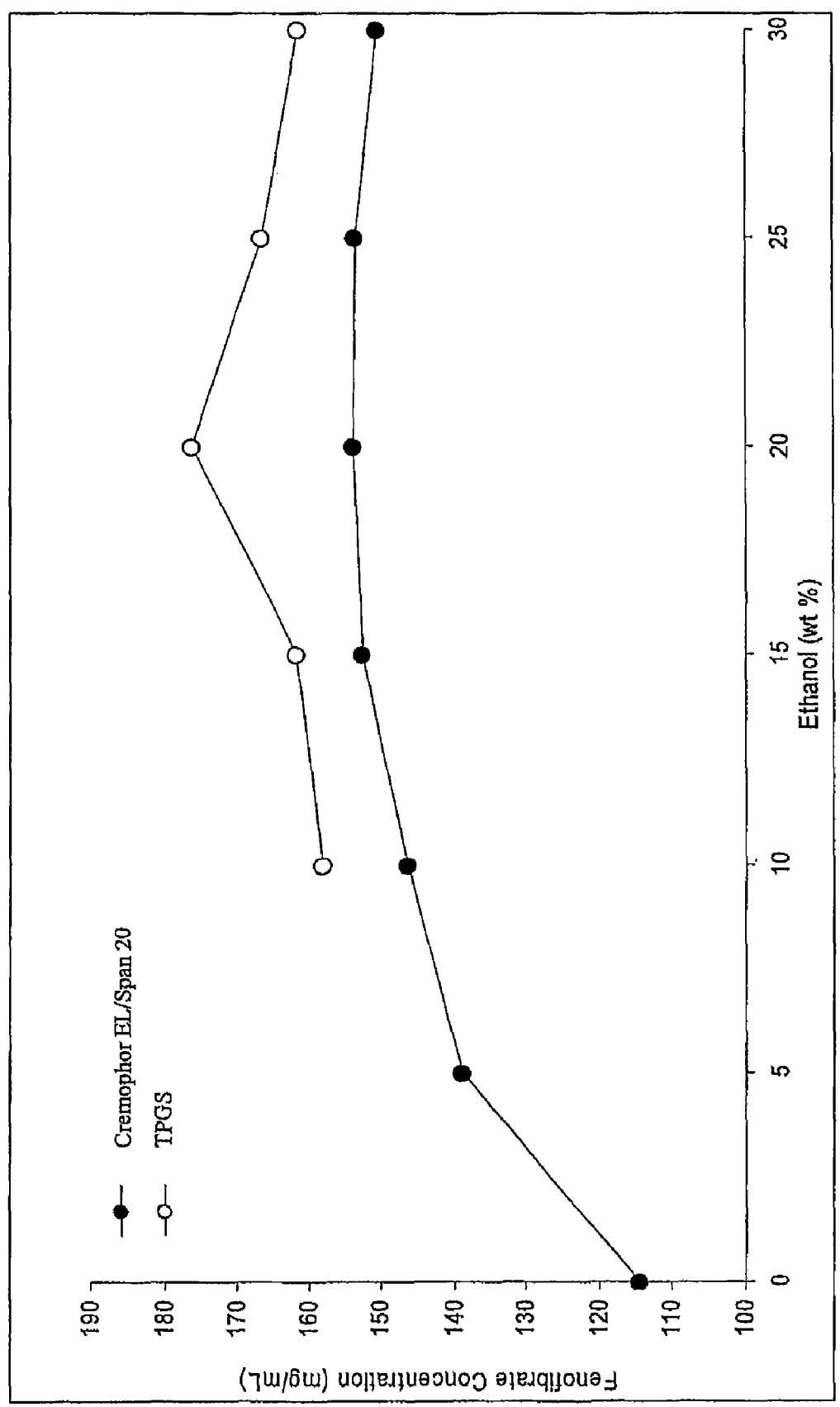
FIG. 4 shows fenofibrate solubility as a function of ethanol concentration.

The solubility of fenofibrate was studied in two surfactant-containing formulations as a function of ethanol concentration. Formulation one comprised E681010:ethanol:Cremophor EL:Span 20, wherein the weight percent of Cremophor EL and Span 20 were each maintained at 10 percent. (For example, the samples contained component weight ratios of 80:0:10:10, 75:5:10:10, 70:10:10:10, 65:15:10:10, 60:20:10:10, 55:25:10:10, and 50:30:10:10.) Note, Span 20 is also known as sorbitan monolaurate. Formulation two contained E681010:ethanol:TPGS, wherein the weight percent of TPGS was maintained at 20 percent. (For example, the samples contained component weight ratios of 70:10:20, 65:15:20, 60:20:20, 55:25:20, and 50:30:20.) Note, TPGS is also known as d-alpha-tocopheryl polyethylene glycol 1000 succinate. FIG. 4 shows the data from zero percent to 30 percent ethanol by weight.

Example 8

Pravastatin Calcium Salt

To a solution of pravastatin Na salt (1.470 g; 3.292 mmol) in water (15.0 mL) was added a solution of calcium acetate (268 mg; 1.70 mmol) also in water (5.0 mL). The resulting solution was concentrated (through evaporation of water via a stream of nitrogen gas) to about 15 mL and cooled to 0° C. A white solid precipitated and was collected via filtration. The filtrate was cooled again to 0° C. which yielded further precipitation. After filtration, the solids were combined and dried in a desiccator. The resultant solid was determined to be pravastatin calcium salt. The resultant salt was a 2:1 pravastatin to calcium salt.

Figure 5:
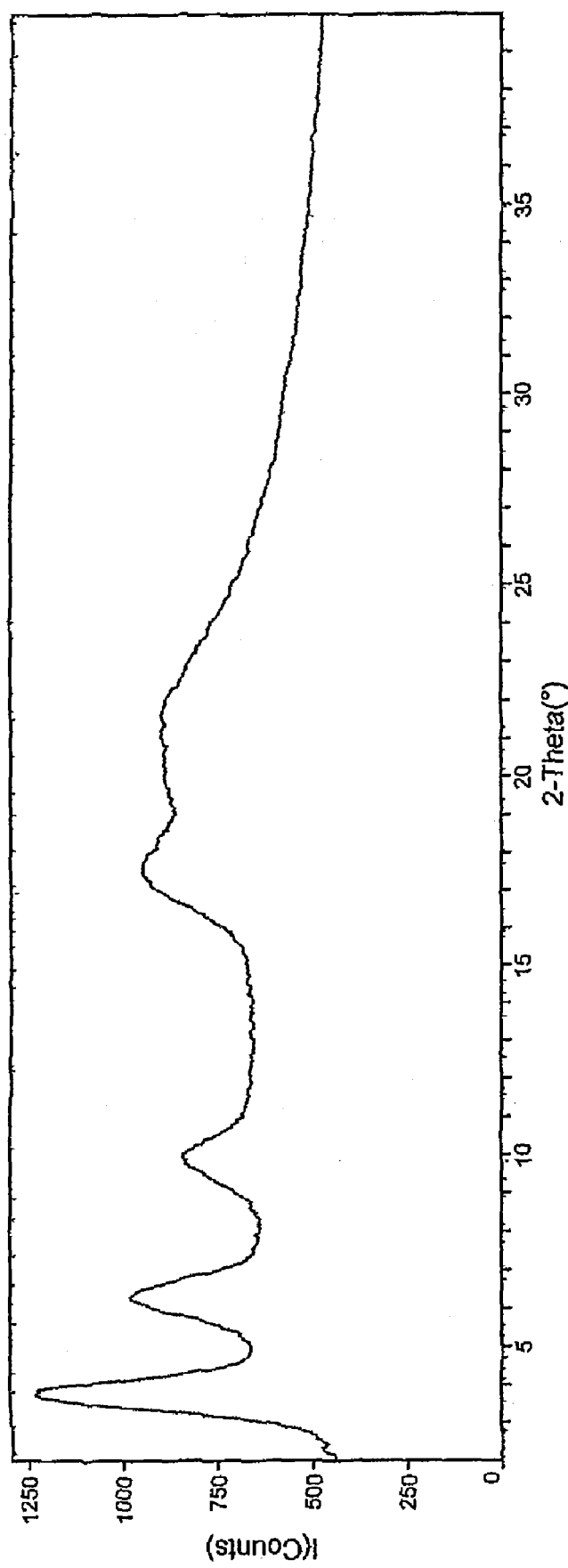
FIG. 5 shows a PXRD diffractogram of a pravastatin calcium salt.

FIG. 5 shows the PXRD diffractogram of the pravastatin calcium salt (Bruker, data as collected). The pravastatin calcium salt can be characterized by any one, any two, any three, or any four or more of the PXRD peaks in FIG. 5. Based on the PXRD diffractogram, the pravastatin calcium salt appears to be weakly crystalline.

Figure 6:
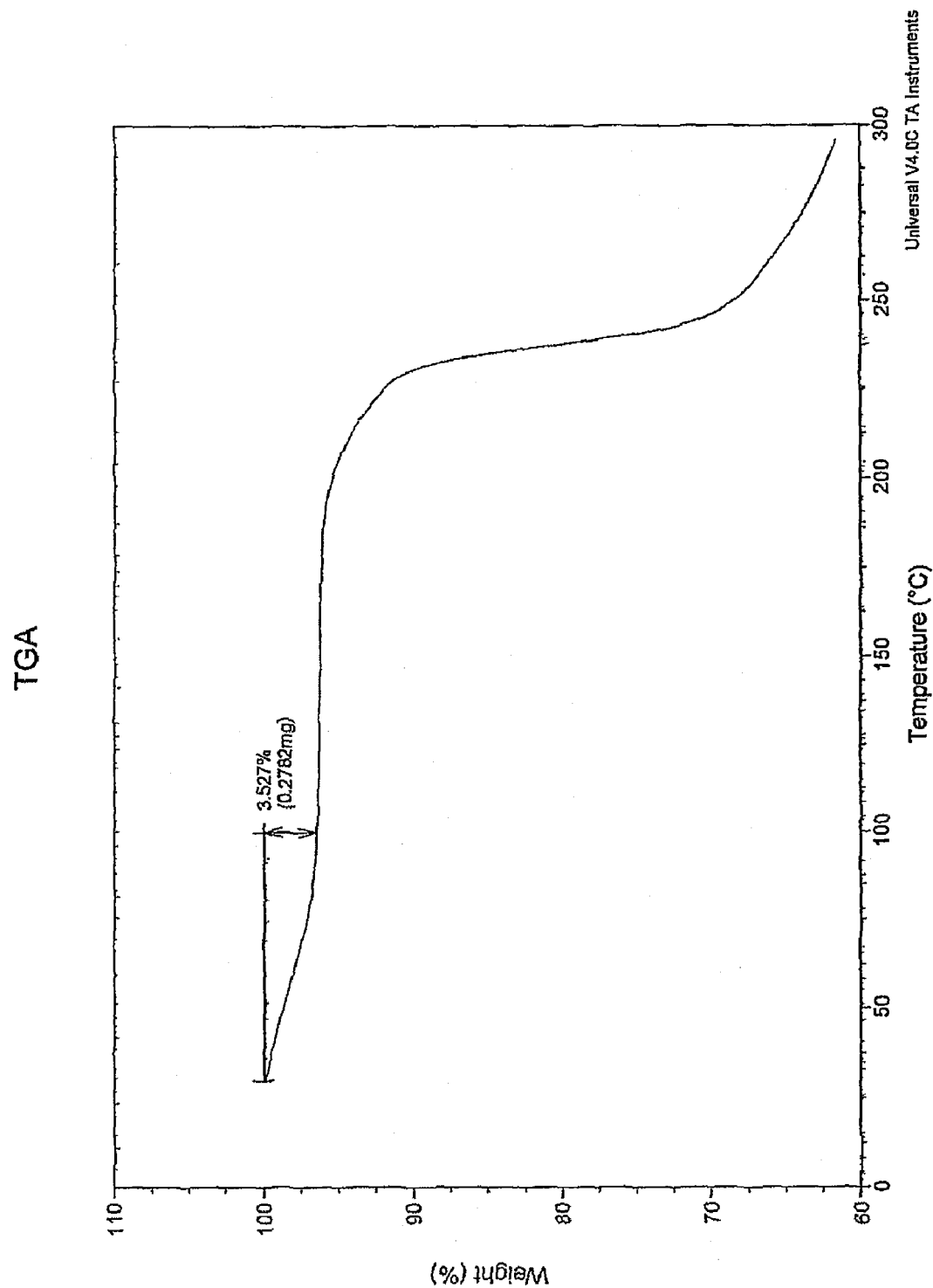
FIG. 6 shows a TGA thermogram of a pravastatin calcium salt.

TGA of the pravastatin calcium salt showed about a 3.5 percent weight loss between about 25° C. and 100° C. (See FIG. 6).

IR spectroscopy was also used to characterize the pravastatin calcium salt. The pravastatin calcium salt can be characterized by any one, any two, any three, any four, any five, or any six or more of the IR peaks in FIG. 7 including, but not limited to, 2360, 1728, 1561, 1444, 1186, 855, and 668 $cm^{-1}$.

Example 9

Qualitative In Vitro Dissolution Experiment

Liquid formulations of the invention comprising fenofibrate were dispersed in various media at 37° C. to determine qualitative in vitro dissolution characteristics of the formulations.

The experimental setup consisted of a 20 mL sample vial in a 37° C. constant temperature water bath. The sample vial contains 15 mL of the desired aqueous medium: water, SGF (simulated gastric fluid), FaSSIF (fasted-state simulated intestinal fluid), or FeSSIF (fed-state simulated intestinal fluid), and a magnetic stir bar. FeSSIF consists essentially of 0.87 g acetic acid, 0.81 g sodium taurocholate, 0.295 g lecithin, 1.187 g sodium chloride, with a pH adjusted to 5.0 with sodium hydroxide and diluted to 100 mL with deionized water. FaSSIF consists essentially of 0.395 g $NaH_2PO_4$, 0.161 g of sodium taurocholate, 0.059 g of lecithin, 0.619 g sodium chloride, with a pH adjusted to 6.5 with sodium hydroxide and diluted to 100 mL with deionized water. SGF consists essentially of 1.0 g Triton X100, 2.0 g sodium chloride, with a pH adjusted to 2.0 with 1M HCl, and dissolved in 1000 mL distilled water. A 150 microliter aliquot of the desired formulation was added to the vial and gently stirred. Vials were briefly removed at certain time intervals and photographed.

Formulations 1-2 were subjected to this procedure and the results noted below were observed.

Formulation 1

A 150 microliter aliquot of a 90:10 mixture (volume/volume) of E463808 and ethanol was mixed with fenofibrate in the weight percentages and amounts set forth in Table 9 below.

TABLE 9

Formulation 1 composition

| Formulation: | Weight (mg): | Weight Percentage: |
|---|---|---|
| E463808 | 724 | 77.6 |
| Ethanol | 69 | 7.4 |
| Fenofibrate | 140 | 15.0 |

The following observations were made with respect to formulation 1. The solubility of fenofibrate in the formulation was 152 mg/mL at 25° C. The solubility of the formulation in FaSSIF was 140 ring/ml. The formulation did not emulsify after 60 minutes and the formulation remained as an oil on the surface of the aqueous medium. Formulation 1 did not show any emulsification in water, SGF, and FeSSIF at 37° C. A pharmaceutical composition comprising this formulation may be appropriately administered to a patient in need of a therapeutic effect.

Formulation 2

A 150 microliter aliquot of a 80:10:10 mixture (volume/volume) of E463808, ethanol, and Labrafac® CC (Gattefosse) medium chain triglyceride ($C_8$-$C_{10}$) carrier was mixed with fenofibrate in the weight percentages and amounts set forth in Table 10 below.

TABLE 10

Formulation 2 composition

| Formulation | Weight (mg) | Weight Percentage |
|---|---|---|
| E463808 | 630 | 68.5 |
| Ethanol | 68 | 7.4 |
| Labrafac ® CC | 82 | 9.0 |
| Fenofibrate | 140 | 15.1 |

The following observations were made with respect to formulation 2. The solubility of fenofibrate in the formulation was 137 mg/mL at 25° C. The formulation did not exhibit emulsification after 60 minutes and the formulation remained as an oil on the surface of the aqueous medium. Formulation 2 did not show any emulsification in water, SGF, and FeSSIF at 37° C. A pharmaceutical composition comprising this formulation may be appropriately administered to a patient in need of a therapeutic effect.

What is claimed is:

1. A formulation comprising a suspension of about 10 to about 25% by weight pravastatin calcium in a solution comprising from about 65 to about 85% by weight an omega-3 fatty acid ethyl ester, from about 5 to about 15% by weight ethanol, from about 10 to about 20% by weight fenofibrate, and optionally from about 10 to about 25% by weight a surfactant.

2. The formulation of claim 1, wherein said omega-3 fatty acid ethyl ester comprises both eicosapentaenoic acid and docosahexaenoic acid.

3. The formulation of claim 2, wherein the eicosapentaenoic acid:docosahexaenoic acid ratio is about 6.8:1.

4. The formulation of claim 2, wherein the eicosapentaenoic acid docosahexaenoic acid ratio is about 2:1.

5. The formulation of claim 2, wherein the eicosapentaenoic acid:docosahexaenoic acid ratio is about 1.5:1.

6. The formulation of claim 2, wherein the eicosapentaenoic acid:docosahexaenoic acid ratio is about 1:1.

7. A method of reducing or treating elevated cholesterol levels, atherosclerosis, hypertriglyceridemia, coronary artery disease, or cerebrovascular disease comprising administering an effective amount of the formulation of claim 1 to a mammal in need thereof.

8. The method of claim 7, wherein said mammal is a human.

9. The formulation of claim 1, comprising about 13% by weight ethanol.

10. The formulation of claim 1, comprising from about 120 mg/ml to about 170 mg/ml fenofibrate at 25° C.

11. The formulation of claim 1, wherein the omega-3 fatty acid ethyl ester comprises 9.7% by weight eicosapentaenoic acid ethyl ester, 71.4% by weight docosahexaenoic acid ethyl ester, and 3.9% by weight other omega-3 fatty acid ethyl esters.

12. The formulation of claim 1, wherein the omega-3 fatty acid ethyl ester comprises 35% by weight eicosapentaenoic acid ethyl ester, 19% by weight docosahexaenoic acid ethyl ester, and 23% by weight other omega-3 fatty acid ethyl esters.

13. The formulation of claim 1, wherein the omega-3 fatty acid ethyl ester comprises 97% by weight eicosapentaenoic acid ethyl ester and 2% by weight other omega-3 fatty acid ethyl esters.

14. The formulation of claim 1, wherein the omega-3 fatty acid ethyl ester comprises 67.8% by weight eicosapentaenoic acid ethyl ester, 9.9% by weight docosahexaenoic acid ethyl ester, and about 9.6% by weight other omega-3 fatty acid ethyl esters.

15. The formulation of claim 1, wherein the pravastatin calcium is crystalline.

16. The formulation of claim 1, wherein the pravastatin calcium exhibits a powder X-ray diffraction pattern as shown in FIG. 5.

Figure 7:
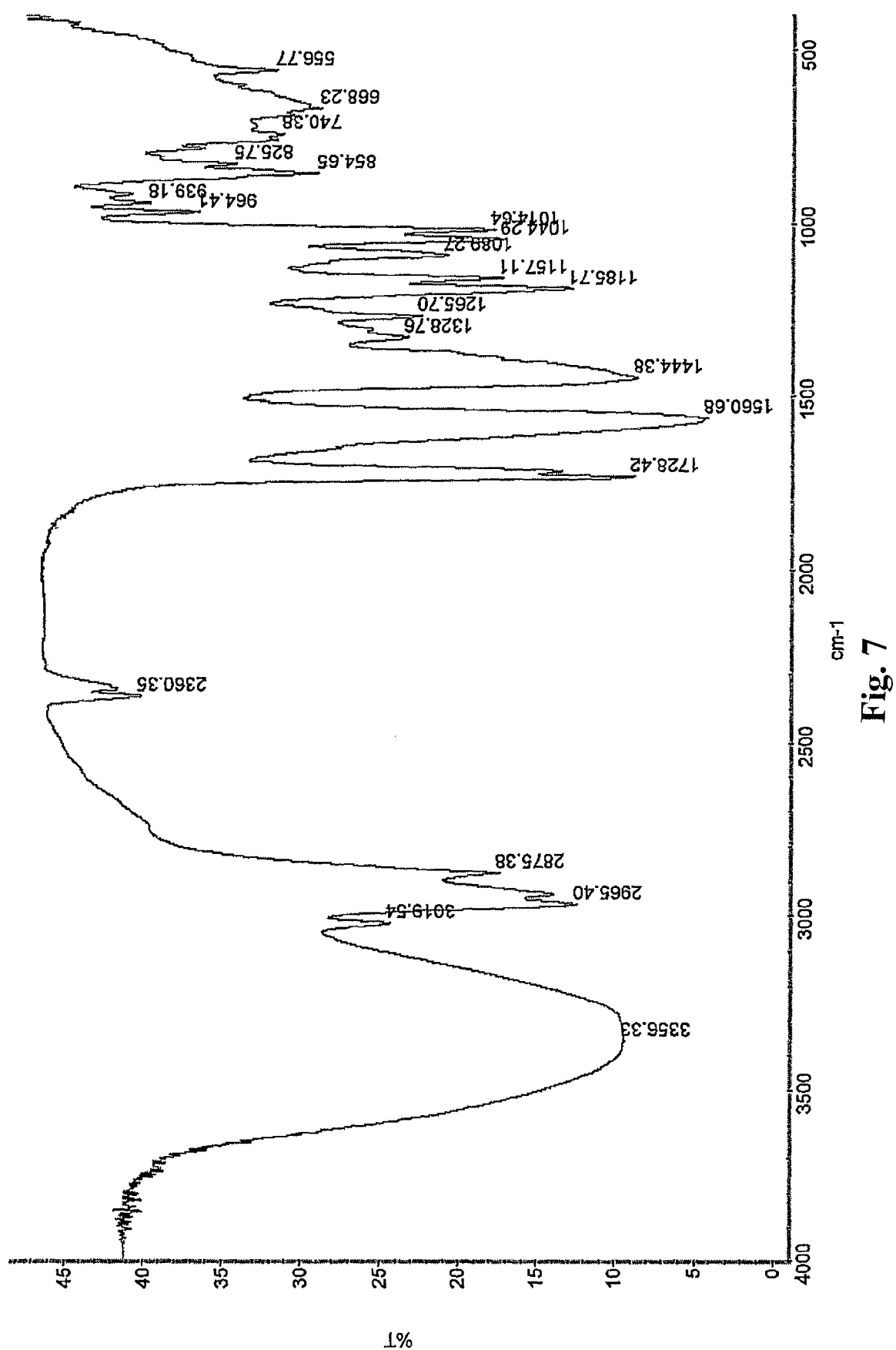
FIG. 7 shows an IR spectrum of a pravastatin calcium salt.

17. The formulation of claim 1, wherein the pravastatin calcium exhibits an IR spectrum as shown in FIG. 7.

18. The formulation of claim 1, wherein the omega-3 fatty acid ethyl ester comprises 46% by weight eicosapentaenoic acid ethyl ester, 38% by weight docosahexaenoic acid ethyl ester, and 8% by weight other omega-3 fatty acid ethyl esters.

* * * * *